United States Patent [19]

Kinkead

[11] 4,315,372
[45] Feb. 16, 1982

[54] CALIPER FOR APPLYING CONSTANT PRESSURE TO AN OBJECT BEING MEASURED

[75] Inventor: Jordan A. Kinkead, Atherton, Calif.

[73] Assignee: Fitness Motivation Institute of America, San Jose, Calif.

[21] Appl. No.: 142,211

[22] Filed: Apr. 17, 1980

[51] Int. Cl.³ .............................................. G01B 5/00
[52] U.S. Cl. .................................................... 33/148 F
[58] Field of Search ................. 33/147, 148, 149, 156, 33/157, 150, 151, 174 D, 455

[56] References Cited

U.S. PATENT DOCUMENTS

| | | | |
|---|---|---|---|
| 1,320,320 | 10/1919 | Crowley | 33/455 |
| 1,630,505 | 5/1927 | Walther | 33/191 |
| 2,559,170 | 7/1951 | Pickett | 33/157 X |
| 3,008,239 | 11/1961 | Lange | 33/143 K X |
| 3,140,546 | 7/1964 | Bartlett | 33/148 F |

FOREIGN PATENT DOCUMENTS 130213 11/1950 Sweden ............................. 33/149 R

OTHER PUBLICATIONS

The Lancet: "Forceps for the Measurement of Skin-fold Thickness" 10/29/1960 p. 962.

Primary Examiner—Harry N. Haroian
Attorney, Agent, or Firm—Gerald L. Moore

[57] ABSTRACT

A constant pressure caliper commonly used to measure the thickness of skin folds and wherein the caliper arms are separated by the actuation of a slide mechanism and are urged together by a constant force spring acting through a linkage that applies a constant force to the caliper arms regardless of the distance the arms are opened. The caliper arms are pivotally connected in a housing such that the lever arm of the force for closing the arms and the lever arm through which the constant tension spring is acting vary proportionally to maintain the closing force constant as the arms are separated different distances.

8 Claims, 5 Drawing Figures

CALIPER FOR APPLYING CONSTANT PRESSURE TO AN OBJECT BEING MEASURED

BACKGROUND OF THE INVENTION

In many applications and especially in the measuring of a skin fold, it is necessary that the caliper arms be urged together by a constant force. For instance in the measuring of a skin fold, the skin is pulled out or pinched and the caliper is used to measure the thickness of the double layer of skin for an indication of the physical condition of the individual. Naturally the skin in being pliable can render different measurements if different pressures are applied to the caliper arms. One past attempt to supply constant pressure calipers is exemplified in the U.S. Pat. No. 3,008,239, issued on Nov. 14, 1961, with Karl O. Lang as inventor. In this patent a pair of caliper arms are mounted on meshing gear wheels with one gear wheel having a tension spring pivotally connected thereto to return it to the closed arm position. An understanding of basic geometry illustrates that there can be a variance in the force exerted on the caliper arms because of the change in the lever arm length through which the spring acts. However the instrument is constructed to minimize this variance for the arm separation for which the caliper is normally used.

The overall purpose of the present invention is to provide a skin fold caliper in which the closing force on the caliper arms remains constant throughout a wide range of separation of the arms.

SUMMARY OF THE INVENTION

A caliper for applying a constant pressure to the surface of an object to measure the object thickness and wherein the caliper includes a housing with a pair of projecting caliper arms of a general C-shape each having a first end pivotally connected within the housing and a second end abutting the other arm to form the caliper tips. A slide mechanism is pivotally connected to each caliper arm at a point between the ends such that movement towards the arms will cause the tips to close and movement away from the arms will open the tips. A contant tension spring acts to apply to the slide mechanism a constant force. This force is in turn transmitted to the arms through lever arms which vary in length as the tips are separated to maintain the actual closing force on the arms constant regardless of the distance the tips are separated. In the preferred embodiment the caliper includes a pistol grip with the slide mechanism being actuated by the pulling of a projectng trigger for easy manipulation with one hand.

DESCRIPTION OF THE INVENTION

Figure 1:
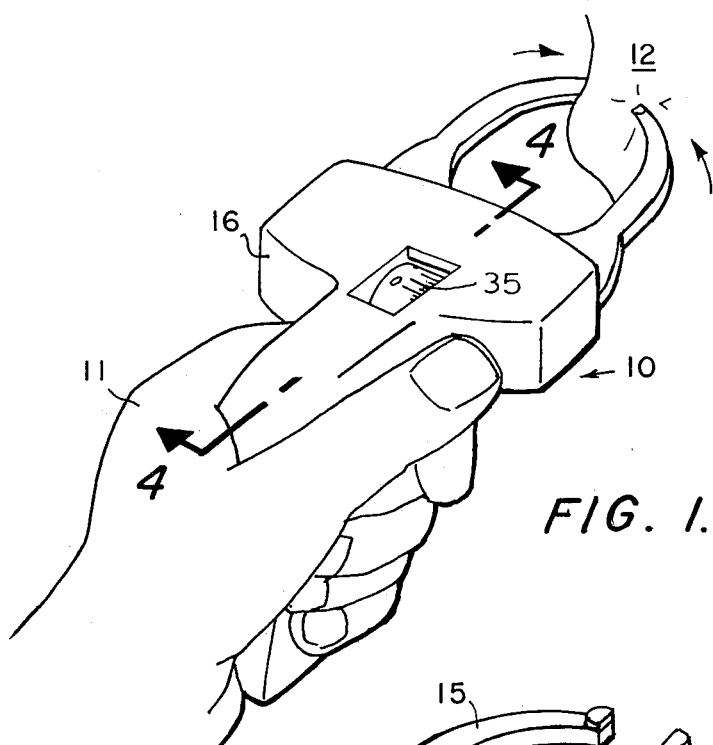
FIG. 1 is a perspective view of the caliper being held in one hand to measure a skin fold.
Figure 2:
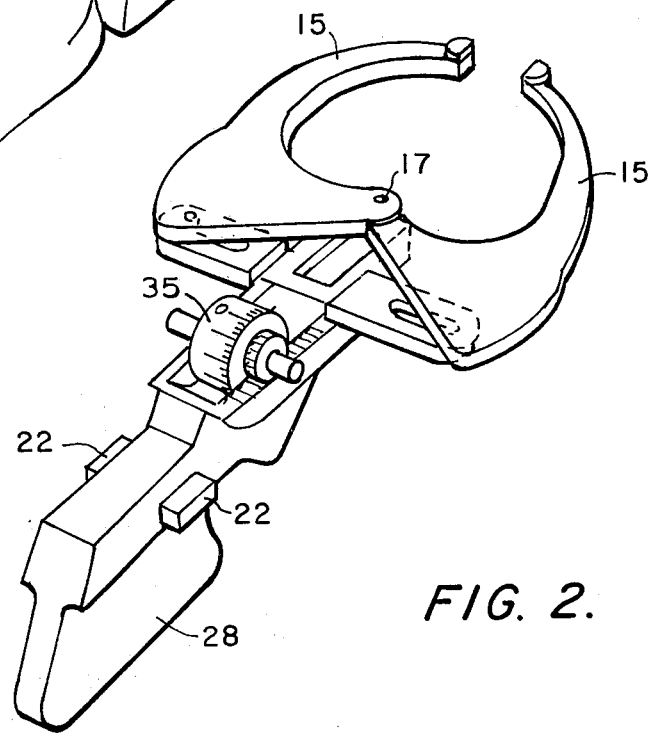
FIG. 2 is a perspective view of the slide and arm assembly with the housing removed.
Figure 3:
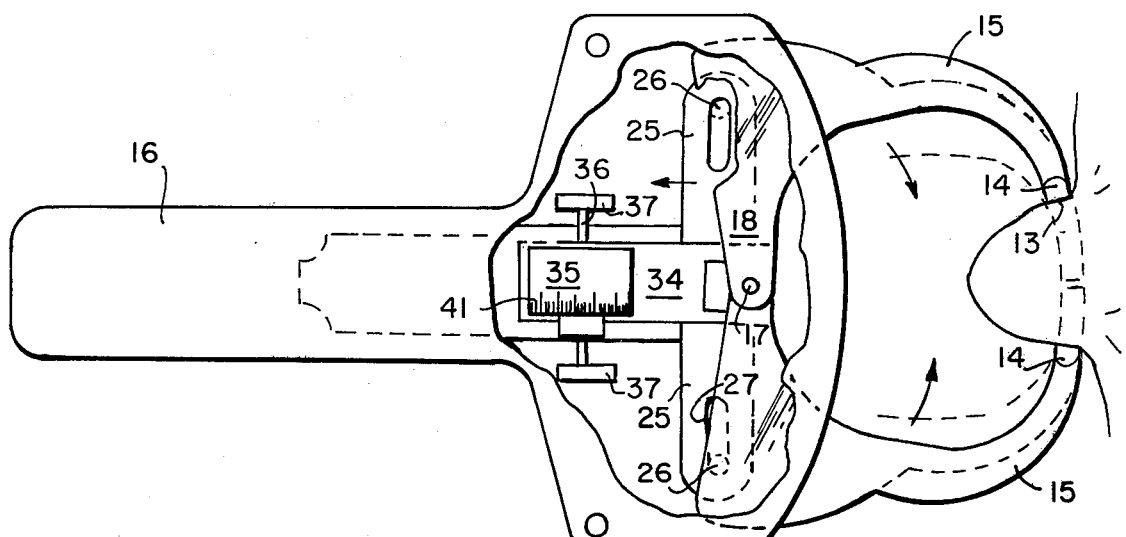
FIG. 3 is a top view with the housing partially broken away to show the internal mechanism of the caliper.

In FIG. 1 is shown a caliper 10 embodying the present invention being held in a left hand 11 for the purpose of measuring the thickness of a skin fold 12. In the normal usage of the invention for this purpose, the fold of skin (usually on the leg or stomach) is pinched or pulled out with one hand while the open caliper tips are fitted thereover and allowed to close. A constant pressure of 10 grams per square millimeter of tip surface is usually applied to determine the thickness of the fold.

Figure 4:
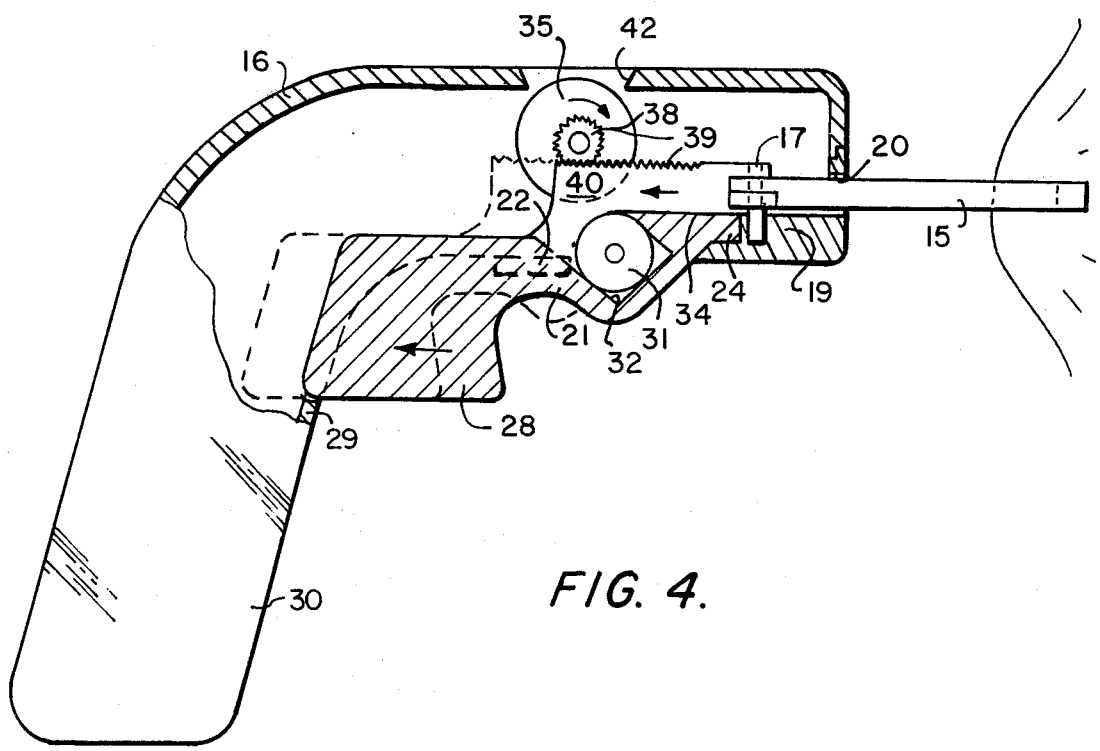
FIG. 4 is a side view with a portion of the housing broken away.

The caliper 10 comprises a housing 16 with projecting caliper arms 15. Each C-shaped caliper is pivotally mounted within the housing on a pin 17 passing through a first end 18 and having one end imbedded in a pedestal 19 (FIG. 4) molded in the housing. Thus the caliper arms are allowed to pivot in a manner to separate the tips 14 by movement within a slot 20 in the end of the housing. The tips 14 are supported on pins 13 to permit a pivoting action and assure that each tip rests flat against the skin.

For pivoting the arms apart, a slide 21 is provided which is supported by the integral rectangular posts 22 which slide along the bottom of the housing, and a forward extension 24 which slides within the housing. The slide is generally T-shaped with a pair of wings 25 extending normal to the forward end and formed with a pair of slots 27 which align with and receive upstanding pins 26 at a point intermediate the ends of the caliper arms. As the slide is moved towards and away from the pin 17, the pins 26 move with the slots 27 and open and close the caliper arms. An integral trigger 28 extending through a bottom slot 29 adjacent the pistol grip 30 of the housing permits single finger actuation of the slide for opening the caliper arms.

To provide a constant force on the caliper arms for biasing the tips 14 together, a constant-force spiral-wound spring 31 is positioned in a recess 32 in the slide. The exposed end 34 of the spring extends forward along the top surface of the slide and includes a hole of sufficient size to fit over the pin 17. This spring end is placed over the pin and the caliper arms are fitted thereover to hold the spring in place. As the slide trigger is pulled back towards the grip 30, the caliper arms 15 are pulled apart and at the same time the wound spring 31 is partially unwound and extended. Release of the trigger 28 allows the spring 31 to return the slide forward thereby closing the caliper arms. The constant tension spring exerts a constant force to return the slide to the forward position and close the caliper arm tips.

Figure 5:
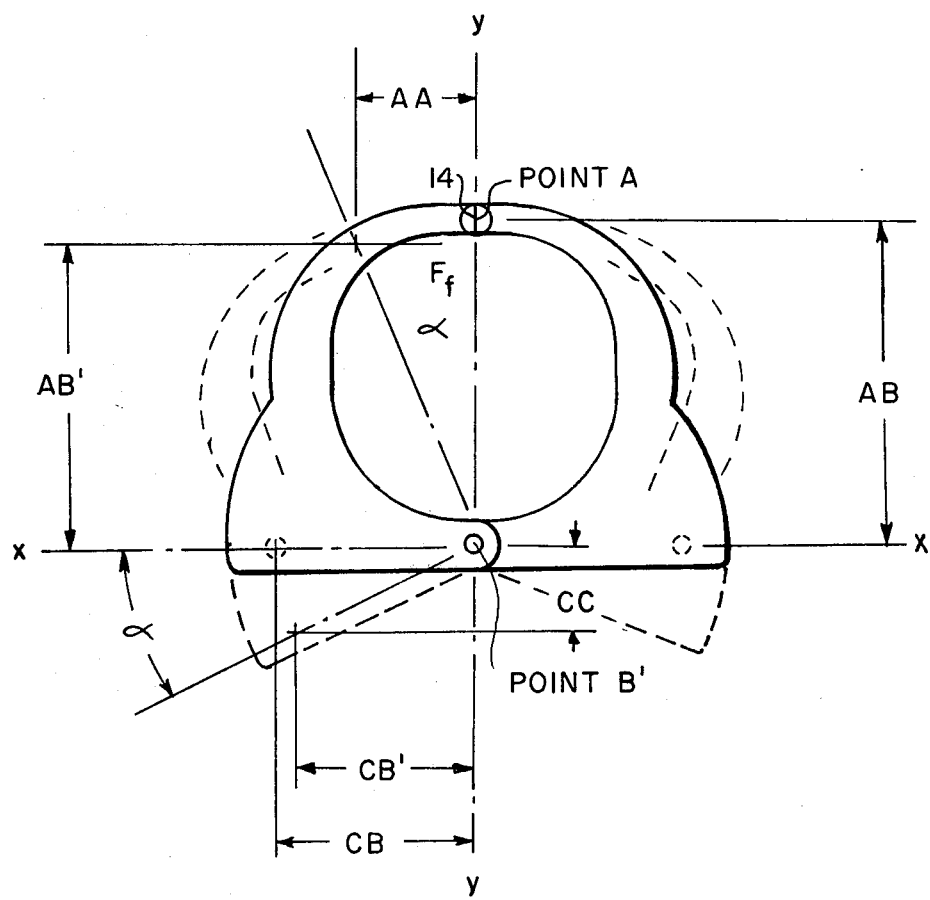
FIG. 5 is a diagram of the caliper arm movement for proving the caliper arm closing force remains constant.

The following is included to show that the force on the caliper arms is constant regardless of the separation distance of the tips (reference the diagram shown in FIG. 5):

Given:

A. The constant force spring acting through the slide 21 applies a constant force $F_s$ acting in a direction parallel to Y—Y axis to close the caliper arms and bring the tips 14 together.

B. The force $F_f$ is always parallel to the X—X axis since the tips 14 pivot about the pin 13.

C. When the pins 26 are moved degrees, the caliper arm tips 14 will move the same number of degrees. (True if pins are on the caliper arms.)

Therefore to show that a constant force is always applied to close the caliper arms, it is necessary to show that $F_s$ (force acting to close the caliper arms) $= KF_f$ since $F_s$ is a constant force.

For an equilibrium condition to exist relative to the stationary caliper arms:

$$F_s \cdot CB' = F_f \cdot AB' \quad (1)$$

Also, $$AB'/AB = \cos \alpha, \text{ or } AB' = AB \cos \alpha \quad (2)$$

$$CB'/CB = \cos \alpha, \text{ or } CB' = CB \cos \alpha \quad (3)$$

Substituting (2) and (3) into (1)

$$F_s \cdot CB \cos \alpha = F_f \cdot AB \cos \alpha \quad (4)$$

cancelling $\cos \alpha$ $$F_s \cdot CB = F_f \cdot AB \quad (5)$$

or $$F_f = F_s \cdot (CB/AB) \quad (6)$$

Since CB and AB are fixed dimensions and therefore equal to a constant K $$F_f = K \cdot F_s \quad (7)$$

or $F_f$ is always a constant proportion of $F_s$ and if $F_s$ is a constant force, $F_f$ is a constant force.

In order to provide a readout of the separation distance between the tips 14, a drum scale 35 is mounted on a shaft 36 extending through openings in a pair of spaced pedestals 38 on the inside of the housing. Also fixed to the shaft 36 is a gear 38 which meshes with a rack 39 formed in the top surface of an elongated land 40 formed integrally with the slide and extending in the direction of the slide movement. As the slide moves back and forth the rack 39 rotates the gear 38 which turns the shaft 36 and the dial 35. Marked on the outer cylindrical surface of the dial are indicia 41 which correspond to the distance between the caliper arm tips resulting from that positioning of the slide. The dial surface is viewed through an opening 42 in the top of the housing 16.

Thus as described there is provided a constant force caliper which is easily manipulated by one hand thereby leaving the other hand free for pinching the skin and placement of the caliper arms. The dial 35 is easily read from the top of the housing to indicate directly the spacing between the arm tips.

The invention claimed:

1. A caliper for applying a constant pressure to the surface of an object to measure the object thickness, said caliper comprising:
   a housing;
   a pair of caliper arms each having a first end pivotally connected to said housing and having a second end abutting the second end of the other caliper arm and separable therefrom by pivoting said arms about the pivotal connections;
   a slide mechanism held on said housing and connected to each such caliper arm by a sliding pivotal connection at a point intermediate the ends; and
   a constant tension spring connected to said slide mechanism to urge said caliper second ends into abutting relationship whereby movement of the slide mechanism will cause the caliper arm second ends to separate and be urged back together by said constant tension spring to measure the thickness of the object therebetween.

2. A caliper as defined in claim 1 wherein said caliper arms are C-shaped with tips pivotally connected to said second ends.

3. A caliper as defined in claim 1 wherein the pivotal connection to said housing is a pin fixed on said housing and extending through each caliper arm first end.

4. A caliper as defined in claim 3 wherein each caliper arm includes a pin positioned intermediate said ends and said slide mechanism includes a slot through which the pin extends to form said pivotal connection therebetween.

5. A caliper as defined in claim 1 wherein said housing includes a pistol grip and said slide includes a trigger to allow the caliper to be held in one hand and the arms to be placed around an object.

6. A caliper for measuring an object thickness, said caliper comprising:
   a housing;
   a pair of caliper arms each having a first end pivotally connected to said housing and having second ends abutting but separable by pivoting said arms about the pivoted connections;
   a slide mechanism held on said housing and connected to each such caliper arm by a sliding pivotal connection at a point intermediate the ends; and
   a spring connected to said slide mechanism to urge said caliper second ends into abutting relationship whereby movement of the slide mechanism will cause the caliper arm second ends to separate and be urged back together by said spring to measure the thickness of an object between said arm second ends.

7. A caliper as defined in claim 6 wherein the caliper arms are pivotally connected to said housing by a pin fixed to said housing and extending through each caliper arm first end.

8. A caliper as defined in claim 6 wherein each caliper arm includes a pin positioned intermediate said ends and said slide mechanism includes a slot therein through which said pin extends to form said pivotal connection therebetween.

* * * * *